United States Patent [19]

Tarjan et al.

[11] Patent Number: 4,475,560

[45] Date of Patent: Oct. 9, 1984

[54] TEMPORARY PACING LEAD ASSEMBLY

[75] Inventors: Peter P. Tarjan; Stanley R. Hess, both of Miami, Fla.

[73] Assignee: Cordis Corporation, Miami, Fla.

[21] Appl. No.: 372,910

[22] Filed: Apr. 29, 1982

[51] Int. Cl.$^{3}$ .......... A61N 1/04

[52] U.S. Cl. .......... 128/785; 128/786

[58] Field of Search .......... 128/784–786, 128/419 P

[56] References Cited

U.S. PATENT DOCUMENTS

| | | | |
|---|---|---|---|
| 3,533,403 | 10/1970 | Woodson | 128/642 |
| 3,749,101 | 7/1973 | Williamson | 128/786 |
| 3,754,555 | 8/1973 | Schmitt | 128/785 |
| 3,814,104 | 6/1974 | Irnich et al. | 128/785 |
| 3,902,501 | 9/1975 | Citron et al. | 128/785 |
| 4,030,508 | 6/1977 | Thalen | 128/786 |
| 4,033,357 | 7/1977 | Helland et al. | 128/419 P X |
| 4,103,690 | 8/1978 | Harris | 128/785 |
| 4,135,518 | 1/1979 | Dutcher | 128/642 |
| 4,236,529 | 12/1980 | Little | 128/785 |
| 4,258,724 | 3/1981 | Balat et al. | 128/785 |
| 4,280,512 | 7/1981 | Karr et al. | 128/785 |
| 4,352,360 | 10/1982 | King | 128/786 |

FOREIGN PATENT DOCUMENTS

| | | | |
|---|---|---|---|
| 2736275 | 2/1979 | Fed. Rep. of Germany | 128/785 |

*Primary Examiner*—Lee S. Cohen

*Attorney, Agent, or Firm*—Henry W. Collins; Thomas R. Vigil

[57] ABSTRACT

The temporary pacing lead assembly (10) includes an electrically conductive flexible wire (14), a terminal member (16) electrically connected to one end of the conductive wire (14), an insulative coating or sheath (24) extending over substantially the entire length of the wire (14) and an electrode (12) electrically connected to the other end of the conductive wire (14). An arrow-shaped anchoring device (34) is carried by the electrode (12) for attaching the electrode (12) to the endocavitary wall of an organ to be stimulated. An anchor release mechanism (62, 60, 90) is coupled to the arrow-shaped anchoring device (34) for subsequent removal of the anchoring device (34) from the endocavitary wall.

21 Claims, 5 Drawing Figures

TEMPORARY PACING LEAD ASSEMBLY

TECHNICAL FIELD

The present invention relates to a temporary pacing lead assembly for delivering electrical stimulation pulses to an organ, and more particularly to an improved temporary pacing lead assembly which includes an anchoring device for affixing a pacing lead of the assembly to the wall of an organ to be stimulated and a release mechanism for subsequently removing the anchoring device from the wall of the organ so that the pacing lead may be removed.

BACKGROUND ART

Heretofore cardiac pacing lead assemblies have generally comprised an electrode and a flexible insulated conductor for connecting the electrode to a cardiac stimulator. The electrode is introduced through the vascular system into a cardiac cavity and is moved into a position to contact the endocavitary wall of the heart. Various types of attaching devices have been utilized to maintain the electrode in a fixed position with respect to the wall to be stimulated. For example, fins and tines on the electrode have been utilized to interlock in the trabeculae within the heart in order to prevent dislodgement of the electrode. With any type of electrode attaching device, there is some probability that the electrode will become displaced from the wall of the heart due to the constrictions of the heart with each heart beat. Accordingly, cardiac pacing electrodes have been designed to positively attach to the wall of a heart. For example, electrodes may include anchoring devices such as fishhook shaped barbs or pinching wires. If the pacing lead and electrode are to be subsequently removed, as is the case when a patient only requires cardiac pacing following an operation, it is desirable that the electrode be removed without risk of damage to the wall of the heart.

One proposal for enabling a cardiac stimulation probe to be anchored firmly in the endocavity wall until the natural formation of fibrosed tissue ensures securement of the probe in place is with the use of a harpoon shaped anchor situated at the end of the probe and made of a solid, biologically compatible or of a material which can be resorbed during a period on the order of three weeks to three months. Such an endocavitary cardiac stimulation probe is disclosed in U.S. Pat. No. 4,258,724.

As will be described in greater detail hereinafter the present invention provides a temporary pacing lead assembly which differs from the previous assemblies and which may be positively affixed to the endocavitary wall of an organ to be stimulated, but which may also be readily removed at any time, without requiring resorption of the anchoring member, from the wall without creating local damage to the portion of the wall where the lead is attached.

DISCLOSURE OF INVENTION

In accordance with the teachings of the present invention, a temporary pacing lead assembly is provided which includes an electrically conductive flexible wire or pacing lead having a terminal electrically connected to one end of the conductive wire and an insulative coating extending over a major portion of the length of the wire. The other end of the conductive wire is connected to an electrode which carries an anchoring member, preferably an arrow-shaped probe, for anchoring the electrode to the endocavitary wall. The pacing lead assembly also includes a release mechanism for withdrawing the anchoring member from the endocavitary wall so that the pacing lead and electrode may be entirely removed from the patient without damage to the wall of the heart.

More specifically, according to the present invention there is provided a pacing lead assembly comprising a pervenous electrode assembly; a terminal member; a flexible conductor electrically coupled between said pervenous electrode assembly and said terminal member; an insulative flexible sheath around said conductor, said sheath extending between said pervenous electrode assembly and said terminal member; means for electrically coupling said terminal member to a pulse generator; said electrode assembly including a tubular electrode having an insulated shank portion and an exposed electrically conductive head portion; an anchoring device associated with said tubular electrode and including an arrowhead; means for extending said anchoring device to an anchoring position outward of said tubular electrode and means for retracting said anchoring device to a retracted, non-anchoring recessed positioned relative to said tubular electrode; said means for retracting said anchoring device including a slot in said electrically conductive head portion into which said arrowhead is retracted and recessed; and means for preventing rotation of said arrowhead relative to said tubular electrode so that said arrowhead will move into said slot on retraction thereof.

BEST MODE FOR CARRYING OUT THE INVENTION

Figure 1:
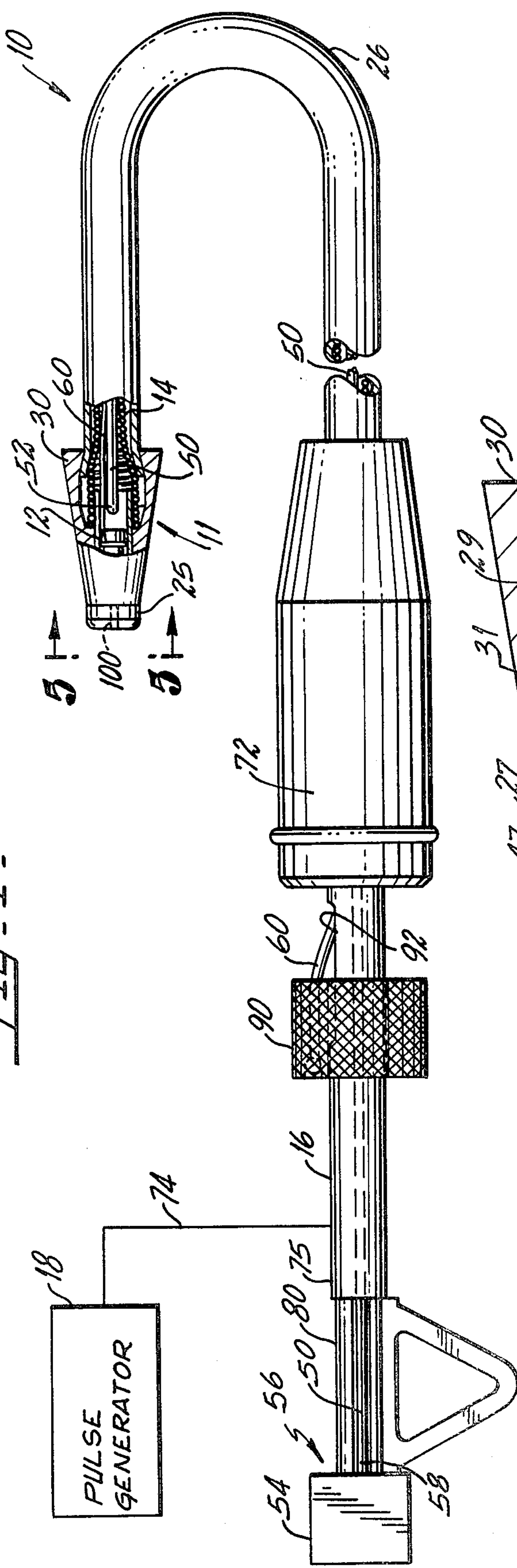
FIG. 1 is a side elevational view of one embodiment of the temporary pacing lead assembly of the present invention with a portion of the electrode of the assembly broken away and shows a pulse generator coupled to the terminal body thereof.

Referring now to the drawings in greater detail, there is illustrated in FIG. 1 the temporary pacing lead assembly of the present invention which is generally identified therein by reference numeral 10 and includes a pervenous electrode assembly 11 having a tubular electrode 12 which is connected by a coiled conductive wire 14 to a tubular terminal member 16. The terminal member 16 is, in turn, electrically connected to a pulse generator 18, such as a cardiac pacer.

The pulse generator 18 applies a pulse electrical signal to the terminal member 16 which is transmitted through the conductive wire 14 to the electrode 12 and the tubular electrode 12 serves to contact the wall of an organ to be stimulated, e.g., an endocardial wall of the heart.

Figure 2:
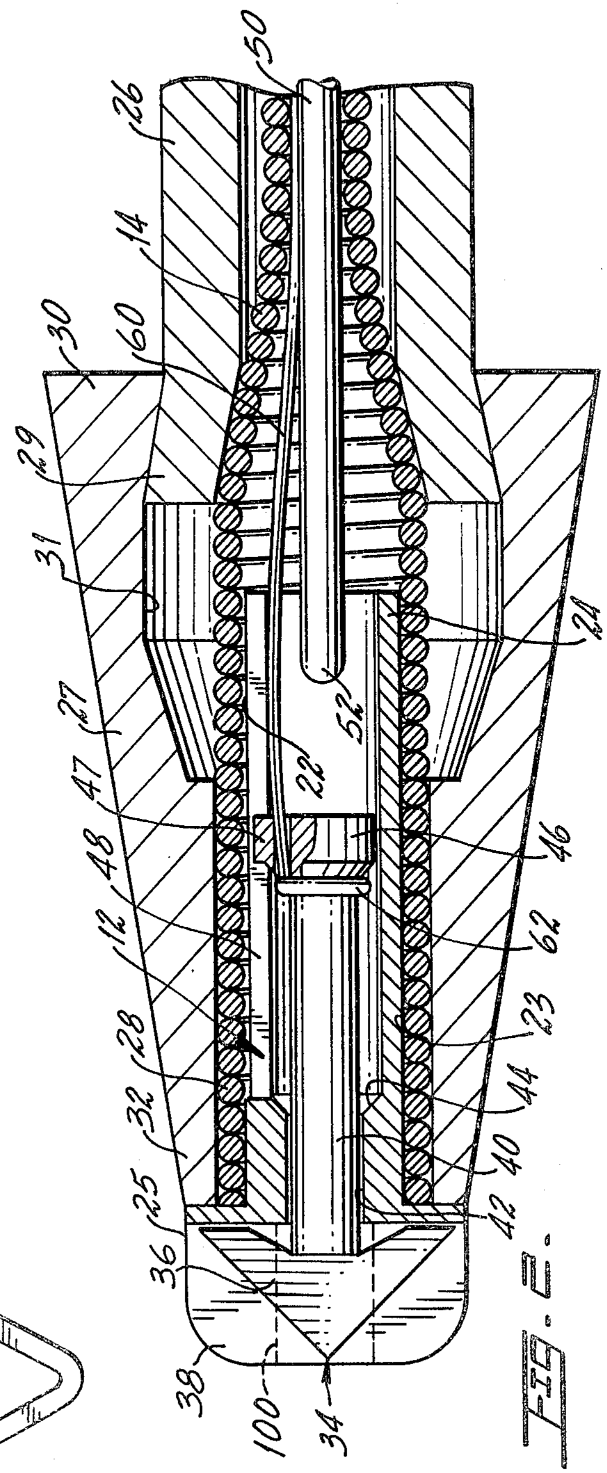
FIG. 2 is a sectional view on an enlarged scale of the electrode shown in FIG. 1 and illustrates in more detail the construction of the electrode with an anchoring member thereof in a withdrawn position.

As is more particularly illustrated in FIG. 2, the tubular electrode 12 is fabricated of a conductive material, for example, platinum. The coiled flexible conductive wire 14 is wrapped around an outer cylindrical surface 22 of a tubular shank portion 23 of the electrode 12 and extends from one end 24 of the shank portion 23 of the electrode 12 to the terminal member 16. The tubular electrode 12 has a slotted, bullet-shaped head portion 25 at the other end of the shank portion 23.

As shown, the coiled flexible conductive wire 12 is encased in an insulative sheath 26 over a major portion of the length thereof.

Also, as shown in FIGS. 1 and 2, the shank portion 23 of the tubular electrode 12 is surrounded by a flared or conical insulating member 27 that extends over the distal end 28 of the coiled conductive wire 14 surrounding the shank portion 23 and in contact with the outer cylindrical surface 22 thereof as well as distal end 29 of the insulative sheath 26.

The insulating member 27 has a base portion 30 with a cavity 31 therein for receiving the distal end 29 of the insulative sheath 26. A head portion 32 of the insulative member 27 abuts the head portion 25 of the tubular electrode 12.

Figures 3, 4, 5:
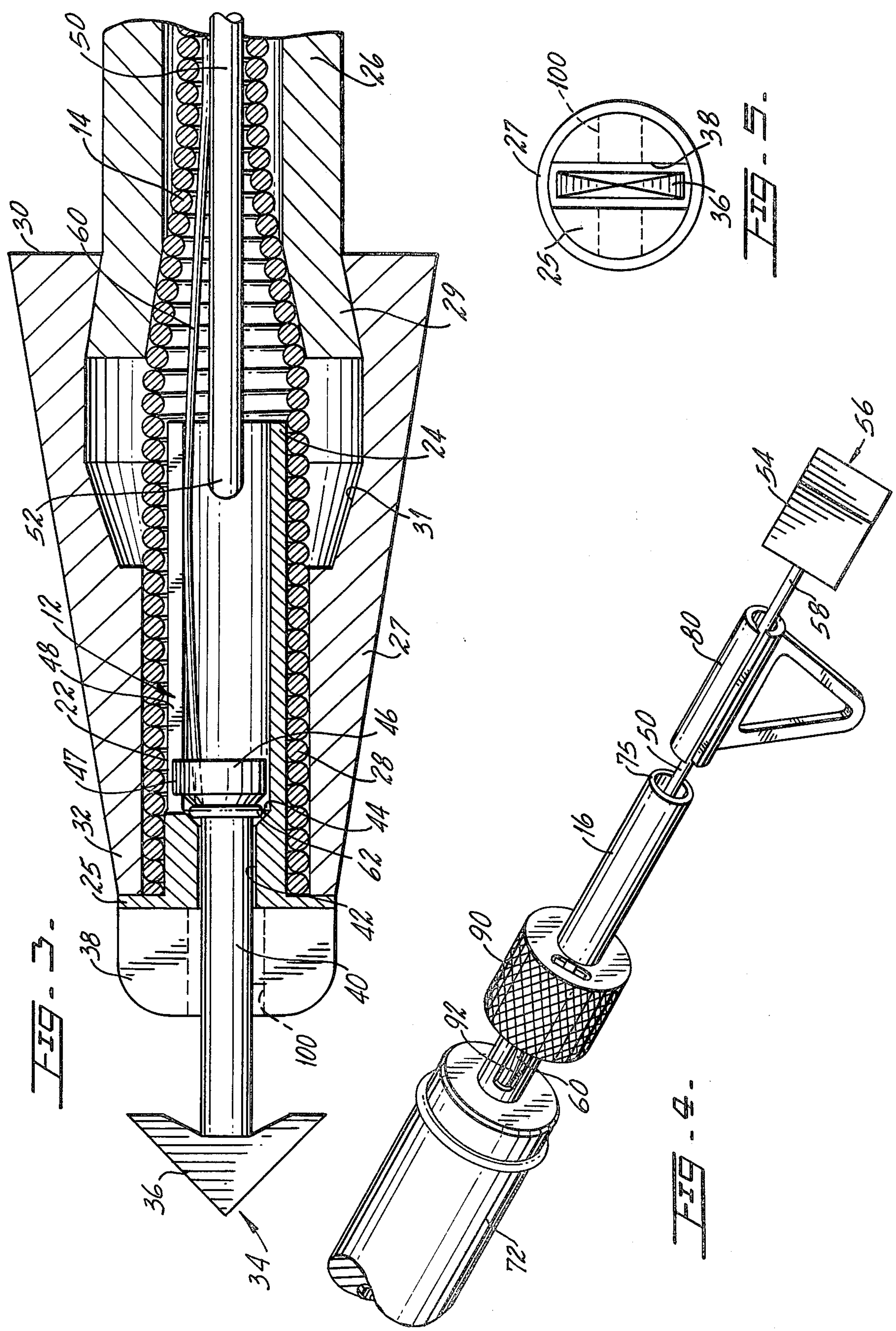
FIG. 3 is a sectional view of the electrode of the pacing lead assembly shown in FIG. 2 with the anchoring member projecting from the end of the electrode.
FIG. 4 is a perspective view of a release mechanism of the assembly connected to the terminal body thereof.
FIG. 5 is a front view of the electrode and anchoring device and is taken along line 5—5 of FIG. 1.

In accordance with the teachings of the present invention, an arrow shaped anchoring device 34 is mounted within the tubular electrode 12. As shown in FIGS. 2 and 3, the anchoring device 34 has an arrowhead 36 which is received within a slot 38 in the bullet shaped head portion 25 of the electrode 12. A shank 40 of the anchoring device 34 extends rearwardly from the arrowhead 36 and is received through and into a tubular cavity 42 in the electrode 12.

The tubular cavity 42 within the shank portion 23 of the electrode 12 is countersunk at 44. The end of the shank 40 opposite arrow head 36 has a retainer flange 46 which has a greater diameter than the shank 40 and which is adapted to seat against the countersunk shoulder 44 of the cavity 42 when the anchoring device 34 is extended from the electrode 12. Such a retainer flange 46 prevents the anchoring device 34 from extending completely out of the tubular electrode 12 as shown in FIG. 3.

With this construction, the arrowhead 36 can be extended from the electrode 12 at the distal end of the pacing lead assembly 10 for affixing the pacing lead assembly 10 to the wall of an organ to be stimulated with the bullet shaped head portion 25 of the electrode 12 in electrical contact with the wall of the organ.

Then, if it is desired to remove the pacing lead assembly 10 from the body, one merely needs to retract the anchoring device 34, namely the arrowhead 36 thereof, into the slot 38 of the bullet shaped head portion 25 of the electrode 12 and then withdraw the pacing lead assembly 10.

Preferably, and as shown, the retainer flange 46 has a rib 47 extending radially outwardly therefrom into a slot 48 in the shank portion 23. In this way, rotation of the anchoring device 34 and more particularly the arrowhead 36 at the outer end thereof is prevented. Longitudinal or axial movement is permitted, however, with rib 47 sliding longitudinally within the slot 48. In this way, the arrowhead 36 which has a short width as shown in FIG. 5 in a direction transverse to the rib 47 and which has a longer width in the radial direction of the rib 47 can be maintained in proper alignment with the slot 38 and properly retracted into the slot 38.

For the purpose of setting the anchoring device 34 into a wall of an organ, a flexible stylet 50 is positioned within the coiled conductive wire 14 as shown. A distal end 52 of the stylet 50 is positioned within the rear end 24 of the tubular shank portion 23 in position to engage the retaining flange 46 to force the anchoring device 34 into the wall of an organ to be stimulated with the rib 47 travelling in the slot 48. This is effected by manually manipulating a plunger block 54 of an anchor setting mechanism 56 shown in FIGS. 1 and 3. As shown, the plunger block 54 is connected to the proximal end 58 of the stylet 50 such that movement of the plunger block 54 against the tubular member 16 will cause the stylet 50 to force the anchor 36 into a wall of an organ.

When it is desired to retract the arrow head 36 into the slot 38, a retracting cable 60 that is tied or secured at end 62 to the shank 40 adjacent the retaining flange 46 can be retracted through the coiled conductive wire 14 for pulling the anchoring device 34 from the extended position thereof shown in FIG. 3 to the retracted position thereof shown in FIG. 2 where the arrow head 36 is received within the slot 38.

Referring now to FIG. 1 a flexure sleeve 72 extends around a portion of the tubular terminal member 16. The proximal end of the sheath 26 and the coiled conductive wire 14 are received in an end of the flexure sleeve 72 wherein the conductive wire 14 is electrically connected to the tubular terminal member 16 which in turn extends out of the flexure sleeve 72 and is connected by a conductor 74 to the pulse generator 18. Extending outwardly from rear end 75 of the tubular terminal member 16 is the proximal end 58 of the flexible stylet 50 which is connected to the plunger block 54.

A slotted tubular spacer 80 is received over the stylet 50 between end 75 of the tubular terminal member 16 and plunger block 54 of the anchor setting mechanism 56. When it is desired to push the distal end 52 of the stylet 50 against the anchoring device 34 for implantation thereof, the spacer 80 is removed and the plunger block 54 is moved against end 75 of member 16.

A cable retaining collar 90 is received over the tubular terminal member 16 and a slot 92 is provided in the tubular terminal member 16 adjacent the flexure sleeve 72 to provide an outlet opening for the proximal end 94 of the retracting cable 60 which is fixed to the collar 90. If it is desired to retract the anchoring device 34 from the wall of the organ, one merely grasps the tubular terminal member 16 in one hand and then pulls the collar 90 with the other hand rearwardly to the left viewing same in FIG. 1 (or to the right viewing same in FIG. 3) to pull the anchoring device 34 rearwardly into the tubular electrode 12 with the arrowhead 36 being withdrawn in proper alignment into nesting engagement with the head portion 25 in the slot 38.

The anchoring device 34 can be made of various biocompatible materials with the preferred materials being nylon or polysulfone.

After the anchoring device 34 has been anchored in an endocavitary wall for a period of time of from 3 weeks to 3 months, fibrous tissue forms around the electrode assembly 11 and secures same in place.

If desired, the arrowhead 36 and/or electrode head 25 can be coated with a collagen attachment factor such as fibronectin.

Of course, if it is desired to retract the electrode assembly 11 and pacing lead assembly 10 after and within the first three weeks of implantation, then this can be done easily by retracting the arrow head 36 into the slot 38 and then withdrawing the whole pacing lead assembly 10 from the patient.

Another material from which the anchoring device 34 can be made is a biologically compatible material which can be resorbed by the endocardial tissue.

Also, if desired, a cross slot 100 shown in phantom in FIGS. 1, 2 and 3 can be provided in the bullet shaped head portion 25 of the tubular electrode for the purpose of increasing the surface area of the head portion 25 of the electrode 12 to minimize electrode polarization.

From the foregoing description it will be apparent that the pacing lead assembly 10 of the present invention has a number of advantages, some of which have been described above and others of which are inherent in the invention.

Also, it will be apparent to those skilled in the art that modifications can be made to the pacing lead assembly 10 of the present invention without departing from the teachings of the invention. Accordingly, the scope of the invention is only to be limited as necessitated by the accompanying claims.

We claim:

1. A pacing lead assembly comprising: a pervenous electrode assembly; a terminal member; a flexible conductor electrically coupled between said pervenous electrode assembly and said terminal member; an insulative flexible sheath around said conductor, said sheath extending between said pervenous electrode assembly and said terminal member; means for electrically coupling said terminal member to a pulse generator, said electrode assembly including a tubular electrode having an insulated shank portion and an exposed electrically conductive head portion; an anchoring device associated with said tubular electrode and including an arrowhead; means for extending said anchoring device to an anchoring position outward of said tubular electrode; and means for retracting said anchoring device to a retracted, non-anchoring recessed position relative to said tubular electrode; said means for retracting said anchoring device including a slot in said electrically conductive head portion into which said arrowhead is retracted and recessed; and means for preventing rotation of said arrowhead relative to said tubular electrode so that said arrowhead will move into said slot on retraction thereof.

2. The pacing lead assembly of claim 1 wherein said head portion has a second slot extending transversely of said first slot for minimizing electrode polarization.

3. The pacing lead assembly of claim 1 wherein said anchoring device includes said arrowhead received in said slot and a shank which extends rearwardly of said arrowhead into said tubular electrode.

4. The pacing lead assembly of claim 3 wherein said tubular electrode has a passageway therethrough which has a cross section at the front end thereof adjacent said head portion slightly larger than the cross section of said shank of said anchoring device and a larger cross section rearwardly of said head portion to form a countersunk shoulder in said passageway facing away from said head portion of said electrode, and wherein said shank of said anchoring device has a retaining flange at the rear end thereof which is adapted to engage and seat against said countersunk shoulder to limit extension of said anchoring device from said electrode assembly.

5. The pacing lead assembly of claim 4 wherein said retaining flange has a rib which extends radially outwardly therefrom and said shank portion of said tubular electrode has a slot therein into which said rib is received thereby to prevent relative rotational movement between said anchoring device and said tubular electrode but permitting relative axial movement between said anchoring device and said tubular electrode, said rib and said slot defining said means for preventing relative rotation of said arrowhead.

6. The pacing lead assembly of claim 3 wherein said arrowhead is defined by two fins diametrically opposite each other with the back edges of the fins being generally perpendicular to the axis of said shank.

7. The pacing lead assembly of claim 1 wherein said flexible conductor is a coiled conductor wire, the distal end thereof being received over and in electrical contact with the outer surface of said shank portion of said tubular electrode, wherein said pervenous electrode assembly includes a frustoconical insulative member which is received around the shank portion of said tubular electrode and over said distal end of said coiled wire conductor the remainder of which extends rearwardly of the electrode assembly like a coiled spring within said sheath to said terminal member, and wherein said frustoconical insulative member has a cavity in the base portion thereof which receives the distal end of said sheath.

8. The pacing lead assembly of claim 1 wherein said extending means include means for pushing said anchoring device into the wall of an organ.

9. The pacing lead assembly of claim 8 wherein said anchoring device includes a shank extending rearwardly of said arrowhead into said tubular electrode and said pushing means include a flexible stylet which is received within said sheath and which has a distal end and a proximal end, and means connected to said proximal end for enabling one to push said distal end of said stylet into engagement with the rear end of said shank of said anchoring device.

10. The pacing lead assembly of claim 1 wherein said retracting means is separate from said extending means.

11. The pacing lead assembly of claim 10 wherein said anchoring device includes a shank extending rearwardly of said arrowhead into said tubular electrode and said retracting means include a retracting cable extending within said sheath and connected at the distal end thereof to said shank of said anchoring device and at the proximal end to a cable retainer which can be manipulated for withdrawing part of said cable from said sheath for retracting said anchoring device.

12. The pacing lead assembly of claim 1 wherein said flexible conductor is a coiled conductor wire which extends like a coiled spring from said pervenous electrode assembly to said terminal member.

13. The pacing lead assembly of claim 1 wherein said anchoring device includes said arrowhead and a shank which extends rearwardly of said arrowhead into said tubular electrode, and said extending means include a flexible stylet extending through said insulative sheath and having a distal end adapted to engage the rear end of said shank of said anchoring device and a proximal end which extends outwardly of said terminal member.

14. The pacing lead assembly of claim 13 wherein said retracting means include a retraction cable received within said sheath and connected at the distal end thereof to said shank of said anchoring device and the proximal end thereof to a cable retainer which can be pulled back a short distance thereby pulling said anchoring device back into its retracted nested position.

15. The pacing lead assembly of claim 14 wherein said terminal member is tubular, said flexible conductor is a coiled conductor wire which extends from the terminal member like a coiled spring within said insulative sheath to said electrode in said pervenous electrode assembly with said flexible stylet extending through said tubular terminal member and through said coiled conductor wire to the pervenous electrode assembly and wherein said cable retainer is in the form of a collar slidably mounted on said tubular terminal member which has a slot therein through which the proximal end of the cable extends for connection to said cable retainer.

16. The pacing lead assembly of claim 1 wherein the exposed head portion of said anchoring device is coated with a collagen attachment factor.

17. The pacing lead assembly of claim 16 wherein said collagen attachment factor is fibronectin.

18. The pacing lead assembly of claim 1 wherein the exposed portion of said electrode is coated with a collagen attachment factor.

19. The pacing lead assembly of claim 18 wherein said collagen attachment factor is fibronectin.

20. The pacing lead assembly of claim 1 wherein said anchoring device includes a shank extending rearwardly of said arrowhead into said tubular electrode and said means for extending said anchoring device and said means for retracting said anchoring device both include and are defined by a flexible stylet which is received within said sheath and which has a distal end and a proximal end, said distal end of said flexible stylet being directly connected to the rear end of said shank of said anchoring device and said proximal end of said stylet being directly connected to means for pushing or pulling said anchoring device relative to said head portion.

21. A pacing lead assembly comprising: a pervenous electrode assembly; a tubular terminal member; a flexible conductor electrically coupled between said pervenous electrode assembly and said terminal member; an insulative flexible sheath around said conductor, said sheath extending between said pervenous electrode assembly and said terminal member; means for electrically coupling said terminal member to a pulse generator; said electrode assembly including a tubular electrode having an insulated shank portion and an exposed head portion; an anchoring device associated with said tubular electrode; means for extending said anchoring device to an anchoring position outward of said tubular electrode and for retracting said anchoring device to a retracted, non-anchoring recessed nested position relative to said tubular electrode; said anchoring device including a proximal shank which extends into said tubular electrode; said extending and retracting means including (a) a flexible stylet extending through said insulative sheath and having a distal end adapted to engage the rear end of said shank of said anchoring device and a proximal end which extends outwardly of said terminal member and (b) a retraction cable received within said sheath and connected at the distal end thereof to said shank of said anchoring device and at the proximal end thereof to a cable retainer which can be pulled back a short distance for pulling said anchoring device back into its retracted nested position; and said cable retainer being in the form of a collar slidably mounted on said tubular terminal member which has a slot therein through which the proximal end of the cable extends for connection to said cable retainer.

* * * * *